United States Patent [19]
Levy

[11] Patent Number: 5,736,328
[45] Date of Patent: Apr. 7, 1998

[54] HYBRIDIZATION ASSAYS FOR DETECTING THE PRESENCE OF AN AIDS-ASSOCIATED VIRUS

[75] Inventor: Jay A. Levy, San Francisco, Calif.

[73] Assignee: Regents of the University of California, Alameda, Calif.

[21] Appl. No.: 443,892

[22] Filed: May 31, 1995

Related U.S. Application Data

[62] Division of Ser. No. 956,682, Oct. 5, 1992, abandoned, which is a continuation of Ser. No. 628,500, Dec. 17, 1990, abandoned, which is a continuation of Ser. No. 433,393, Nov. 7, 1989, abandoned, which is a continuation of Ser. No. 80,635, Jul. 31, 1987, abandoned, which is a continuation of Ser. No. 641,167, Aug. 15, 1984, Pat. No. 4,716,102.

[51] Int. Cl.$^6$ .................. C12Q 1/70; C12Q 1/68; C07H 21/02; C07H 21/04; C07H 21/00
[52] U.S. Cl. .................. 435/6; 435/5; 536/231; 536/24.3; 536/25.32
[58] Field of Search ............... 536/23.1, 24.3, 536/25.32; 435/5, 6

[56] References Cited

U.S. PATENT DOCUMENTS

| | | | |
|---|---|---|---|
| 4,520,113 | 5/1985 | Gallo et al. | 436/504 |
| 4,716,102 | 12/1987 | Levy | 435/5 |
| 4,725,669 | 2/1988 | Essex et al. | 530/322 |
| 4,772,547 | 9/1988 | Heimer et al. | 435/5 |
| 5,089,386 | 2/1992 | Stackebrandt et al. | 435/6 |

FOREIGN PATENT DOCUMENTS

| | | | |
|---|---|---|---|
| 0 138 667 | 9/1995 | European Pat. Off. | G01N 33/571 |
| WO 86/04613 | 8/1986 | WIPO | C12Q 1/70 |

OTHER PUBLICATIONS

Gelmann et al. "Proviral DNA of a retrovirus, Human T–Cell Leukemia Virus, in Two Patients with AIDS" Science, vol. 220, pp. 862–865, May 1983.

Poiesz, B. et al., "Detection and Isolation of Type C Retrovirus Particles From Fresh and Cultured Lymphocytes of a Patient With Cutaneous T–Cell Lymphoma" *Proc. Natl. Acad. Sci.* 77:7415–7419 (1980).

Barre–Sinoussi, F. et al., "Isolation of a T–Lymphotropic Retrovirus From a Patient at Risk for Acquired Immune Deficiency Syndrome (AIDS)" *Science* 220:868–871 (1983).

Pape, J. et al., "Characteristics of the Acquired Immunodeficiency Syndrome (AIDS) in Haiti" *New England J. Medicine* 309:945–950 (1983).

Gallo, R. et al., "Frequent Detection and Isolation of Cytopathic Retroviruses (HTLV–III) from Patients with AIDS and at Risk for AIDS" *Science* 224:500–503 (1984).

Montagnier, L. et al., "A New Human T–Lymphotropic Retrovirus: Characterization and Possible Role in Lymphadenopathy and Acquired Immune Deficiency Syndrome" *Coldspring Harbor Symposium* pp. 363–379 (1984).

Popovic, M. et al., "Detection, Isolation, and Continous Production of Cytopathic Retroviruses (HTLV–III) from Patients with AIDS and Pre–AIDS" *Science* 224:497–500 (1984).

(List continued on next page.)

*Primary Examiner*—Ardin H. Marschel
*Assistant Examiner*—Jezia Riley
*Attorney, Agent, or Firm*—Karl Bozicevic; Bozicevic & Reed

[57] ABSTRACT

A newly discovered family of AIDS-associated viruses, designated ARV, is described. The viruses were isolated from AIDS patients from San Francisco and (a) are type D retroviruses; (b) have Mg$^{++}$-dependent reverse transcriptase activity; (c) induce human multinucleated cells without immortalizing the cells; (d) are replicable in HUT-78 human T cells; and (e) induce viral protein(s) in HUT-78 that binds to Ig from AIDS patients. The infected HUT-78 cells and immunogenic polypeptides derived from the viruses are useful for diagnosing AIDS.

5 Claims, 1 Drawing Sheet

OTHER PUBLICATIONS

Luciw, P. et al., "Molecular Cloning of AIDS-associated Retrovirus" *Nature* (1984) 312:760–763.

Vilmer, E. et al., "Isolation of New Lymphotropic Retrovirus From two Siblings With Haemophilia B, One With Aids" *The Lancet* (Apr. 7, 1984) pp. 753–757.

Hahn, B. et al., "Molecular Cloning and Characterization of the HTLV–III Virus Associated with AIDS" *Nature* (1984) 312:166–169.

Barin, F. et al., "Virus Envelope Protein of HTLV–III Represents Major Target Antigen for Antibodies in AIDS Patients" *AIDS: Papers from Science* (Kulsted, ed.) May 31, 1985, pp. 478–483.

Rabson, A. and Martin, M., "Molecular Organization of the AIDS Retrovirus" *Cell* (1985) 40:477–480.

Levy, J. et al., "AIDS–Associated Retroviruses (ARV) Can Productively Infect Other Cells Besides Human T Helper Cells" *Virology* 147:441–448 (1985).

Sanchez–Pescador, R., "Nucleotide Sequence and Expression of an AIDS–Associated Retrovirus (ARV–2)" *AIDS: Papers from Science* (Kulsted, ed.) Feb. 1, 1986, pp. 410–427.

Myers et al., (eds), Human Retrovirus and AIDS (1988).

HYBRIDIZATION ASSAYS FOR DETECTING THE PRESENCE OF AN AIDS-ASSOCIATED VIRUS

This application is a divisional of application Ser. No. 07/956,682, filed Oct. 5, 1992, now abandoned, which is a continuation of application Ser. No. 07/628,500, filed Dec. 17, 1990, now abandoned, which is a continuation of application Ser. No. 07/433,393, filed Nov. 7, 1989, now abandoned, which is a continuation of application Ser. No. 07/080,635, filed Jul. 31, 1987, now abandoned, which is a continuation of application Ser. No. 06/641,167, filed Aug. 15, 1984, now U.S. Pat. No. 4,716,102 (issued Dec. 29, 1987), to which we claim priority under 35 U.S.C. § 120 and which are incorporated herein by reference in their entirety.

REFERENCE TO GOVERNMENT GRANT

This invention was made with Government support under grant no. CA-34980 awarded by the National Institutes of Health. The Government has certain rights in this invention.

DESCRIPTION

1. Technical Field

This invention relates to the diagnosis and treatment of acquired immune deficiency syndrome (AIDS). More specifically it relates to a newly discovered family of AIDS-associated viruses and the use of those viruses or materials derived from them to diagnose and/or treat AIDS.

2. Background Art

AIDS is known to have affected thousands of individuals worldwide. It is prevalent particularly in populations of male homosexuals. Also many instances of unexplained chronic lymphadenopathy may be caused by the same pathogenic agent that causes AIDS.

Other investigators have reported AIDS-associated viruses. Pope, J. W., et al, *N Engl J Med* (1983) 309:945 and others have reported isolating a human retrovirus designated HTLV-I from AIDS patients. HTLV-I, which is associated with human T cell leukemia, has a type C morphology by electron microscopy (EM), can immortalize T cells, and is primarily cell-associated (Poiesz, B. J., et al, *PNAS* (1980) 77:7415). Barré-Sinoussi, F., *Science* (1983), Montagnier, J. C., et al, Cold Spring Harbor Symposium (1984) in press, and Vilmer, E., et al, *Lancet* (1984) i:753 have found another retrovirus, LAV, in AIDS patients. LAV, which was isolated initially from the lymph node of a patient with lymphadenopathy, has a type D morphology by EM, causes cytopathic changes in T cells, and is infectious in culture fluids. Popovic, M. G., et al, *Science* (1984) 224:497 and Gallo, R. C., et al, *Science* (1984) 224:500 report a third retrovirus, HTLV-III, that is present in patients with AIDS and related syndromes. HTLV-III shows some cross-reactivity with the other HTLV viruses, but, like LAV, has a type D morphology by EM and causes cytopathic changes in lymphocytes.

The present invention concerns a family of AIDS-associated retroviruses that has been isolated from a population of homosexual AIDS patients in San Francisco.

Disclosure of the Invention

The newly discovered family of AIDS-associated viruses have been designated ARV. These viruses are believed to be similar to but distinct from LAV.

In one aspect the invention concerns purified AIDS-associated retroviruses (ARV), which are characterized by:

(a) being of type D morphology by electron microscopy;

(b) having $Mg^{++}$-dependent reverse transcriptase activity;

(c) being capable of inducing human multinucleated cells without immortalizing the cells;

(d) being capable of replicating in HUT-78 human T cells; and (e) inducing viral protein(s) in HUT-78 that is recognized by immunoglobulins from AIDS patients.

A second aspect of the invention relates to immortal human T cell lines, preferably the human T cell line HUT-78, chronically infected with an ARV virus, preferably ARV-2.

A third aspect of the invention concerns a method of detecting anti-ARV antibodies in a sample of an immunoglobulin-containing body fluid of a patient comprising:

(a) incubating at a pH of about 7.2 to about 7.4 the chronically infected T cell line in a fixed form or an immobilized (solid-phase) immunogenic ARV polypeptide with the sample under conditions that promote antigen-antibody binding;

(b) thereafter separating the cells or solid phase from the body fluid and washing the cells or solid phase to remove any residual unbound body fluid therefrom;

(c) incubating the washed cells or solid phase with a labeled antibody to human Ig under conditions that promote antibody-antigen binding;

(d) thereafter separating the cells or solid phase from the labeled antibody and washing the cells or solid phase to remove unbound labeled antibody therefrom; and (e) detecting immune complexes that include said anti-ARV antibodies on or in the cells or solid phase via the label.

Other aspects of the invention concern kits for carrying out the above assay method, reverse-transcribed DNA of the genomic RNA of an ARV virus, fragments of such DNA, labeled embodiments of the DNA or DNA fragments that are useful as DNA hybridization probes, DNA hybridization and cytohybridization assays for detecting ARV virus that employ the labeled DNA probes, and synthetic expression vectors and replicons that include such DNA or fragments thereof that are useful for reproducing the DNA and expressing the DNA in transformed host cells or organisms so as to produce ARV polypeptides.

Still other aspects of the invention relate to: methods of preparing antibodies to ARV that involve immunizing host animals with ARV; and AIDS vaccines whose immunogenic agent is an ARV polypeptide.

MODES FOR CARRYING OUT THE INVENTION

Figure 1:
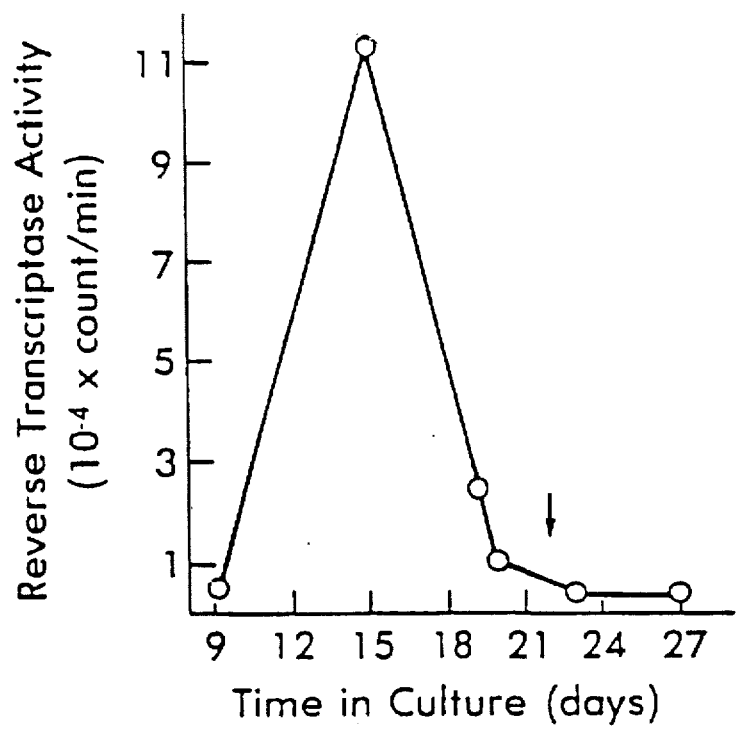
FIG. 1 is a graph showing the $Mg^{++}$-dependent reverse transcriptase activity of the virus detected in peripheral mononuclear cell (PMC) cultures.

The retroviruses of the invention were obtained from PMC samples (primarily from patients in the early stages of disease) or bone marrow samples of homosexual AIDS patients from San Francisco, Calif., USA. The PMCs were obtained from heparinized blood by Ficoll-Hypaque gradient centrifugation followed by washing. The PMCs were cultured by plating in a liquid growth medium (RPMI 1640 supplemented with 10% fetal calf serum and antibiotics) at $2\times10^6$ cell/ml. Lymphocyte stimulaters such as phytohemagglutinin and IL-2, were added to the medium to stimulate lymphocyte proliferation. Polybrene (1 μg/ml) was added to enhance virus spread to fresh cells. After a week of culture surviving cells were primarily of T cell lineage. Virus-containing cultures were identified by screening culture supernatants for $Mg^{++}$-dependent reverse transcriptase (RT) activity.

Cell free virions exhibiting such RT activity were isolated from the supernatants by sucrose gradient centrifugation, with ARV particles banding at 1:14 to 1:16 g/ml.

Characterization of Viruses

The isolated viruses induce multinucleated cells in lymphocyte cultures without immortalizing the cells. Morphology typing of the viruses by EM showed them to be type D retroviruses. Budding forms showed early features of both type C and type D retroviruses, but only mature type D retroviruses were observed in the cultures. Cultures infected with the isolated viral particles reacted with sera from AIDS patients from San Francisco and elsewhere and with anti-LAV sera.

Establishment of ARV Viruses in Continuous Culture

The human T cell lines MOLT-4 (ATCC CRL 1582), CCRF-CEM (ATCC CCL 119), and HUT-78 (obtained from A. Gazdar, Bethesda, Md.) were cultured in RPMI 1640 supplemented with serum, antibiotics, polybrene and anti-human alpha interferon. ARV were then added. The MOLT-4 and CCRF-CEM lines could not be infected successfully under these conditions but the HUT-78 line replicated the viruses in substantial titer. The resulting chronically the infected HUT-78 variants are useful for propagating the viruses, as a source of viral components (e.g., nucleic acids, envelope proteins) and for use in immunoassays for detecting anti-ARV antibodies in Ig-containing samples (typically sera) of patients and other individuals.

A sample of HUT-78 infected with an ARV designated ARV-2 (described below) was deposited at the American Type Culture Collection, 12301 Parklawn Drive, Rockville, Md., USA, on 9 Aug. 1984 under accession number CRL 8597. This deposit was made under the Budapest Treaty and will be maintained and made available in accordance with the provisions thereof.

Immunoassays Using HUT-78 Cells or Immobilized ARV Polypeptides

In immunoassays for anti-ARV antibodies, infected HUT-78 cells or polypeptides that define the immunogenic determinants of ARV immobilized on a solid phase are incubated with a sample of the patient's plasma or serum that has been heat-treated (e.g., heated to 56° C. for approximately ½ hr) to inactivate complement. The HUT-78 cells are fixed beforehand such as by treatment with cold acetone for about 15 min followed by air drying or treatment with 3% paraformaldehyde. The incubation is carried out under conditions that permit and promote antigen-antibody binding. The incubation will typically be carried out at physiological temperature (~37° C.), and a pH of 7.2 to 7.4, preferably 7.3. The incubation time is preferably about ½ hr. After the incubation the cells or solid phase are separated from the sample-containing medium and washed to remove any unbound sample. The cells or solid phase are then resuspended in a medium containing a labeled anti-human Ig antibody using the same or similar incubation conditions. After this second incubation, the cells or solid phase are separated from the medium containing the labeled antibody and washed to remove unbound labeled antibody. The presence of immune complexes in/on the cells or solid phase are detected via the label. The mode of detection will depend upon the nature of the label. Radionuclide labels, such as $^3H$ or $^{125}I$, will be detected by scintillation counting. Flourochrome labels, such as a fluorescein isothiocyanate, will be detected by subjecting the cells or solid phase to excitation energy and observing the resulting fluorescence using a fluorescent microscope. Enzyme labels, such as peroxidases, are detected by incubating the cells or solid phase in a substrate-containing medium and detecting enzyme activity through spectrophotometric measurements of the medium. Other labels may be used as is known in the art.

Kits for carrying out the above-described assay contain the following components: fixed cells on a support such as a slide or cover slip or immunogenic ARV polypeptide bound to a solid phase, such as a cellulose derivative, polystyrene, beaded agarose, cross-linked dextrans, glass, and the like; incubation medium buffered to the desired pH; positive and negative antibody controls; and labeled anti-human Ig antibody. The kits will also typically contain instructions and, in the case of enzyme assays, substrates. Conventional techniques for packaging the kit and its components may be used.

DNA Derived from ARV

ARV-derived polynucleic acid for use in making probes may be obtained from ARV particles or chronically infected HUT-78 cells. Nucleic acids are liberated from the particles or cells, isolated, and digested with one or more restriction enzymes to produce nucleic acid fragments of appropriate size. Particular fragments may be isolated from the digest by gel electrophoresis, if desired. The desired fragments may be replicated by cloning them into a suitable vector (prokaryotic or eukaryotic) to form a replicon. A suitable host is then transformed with the replicon and transformants are propagated to produce copies of the virus-derived nucleic acid fragment. The fragments may be recovered from the host by extracting nucleic acids from the transformants, restricting the nucleic acids with the same endonuclease(s) used previously and resolving the digest, such as by electrophoresis, to isolate the desired fragment(s).

The fragments may be labeled by conventional techniques. The nature of the label and degree of labeling are not critical, depending on the sensitivity that is desired. Radionuclides, fluorochromes and enzymes (e.g., biotin) may be used. $^{32}P$ is a preferred label. The fragments may be labeled with $^{32}P$ by nick translation with a $\alpha$-$^{32}P$-dNTP or other $^{32}P$ labeling procedure.

Hybridization Assays Using Labeled DNA Derived from ARV

Samples of lymphocytes, such as peripheral blood lymphocytes (PBL) or splenocytes from patients may be used in the hybridization assay. PBLs are preferred because they are convenient to obtain.

Conventional nucleic acid hybridization techniques are used in the assay. The cells may be applied to the support, such as a nitrocellulose filter, and lysed in place with a cytolytic agent such as 0.1 to 1M NaOH to liberate nucleic acid. Alternatively, the cells may be lysed beforehand and the lysate applied to the support. If the lysing agent is not one that also denatures the liberated nucleic acids, the lysate is further treated with a nucleic acid denaturant such as DNAase/RNAase. Following denaturation the denaturant is neutralized with buffer. The denatured (single-stranded) nucleic acids are then immobilized (fixed) on the support. When the support is a nitrocellulose filter, fixation is accomplished by treating the denatured nucleic acid-bearing filter with a high salt concentration (2–4M NaCl) buffer and the filter is then dried at elevated temperatures, typically 70°–80° C., for several hours.

The single-stranded nucleic acid fixed on the support is then hybridized with the probe. Before hybridication it may be desirable to pretreat the filter with denatured nonviral-derived DNA (i.e., an ssDNA that will not hybridize to the probe). Such pretreatment saturates binding sites on the filter and prevents nonspecific binding of the probe to the filter. This technique is well known and is commonly called "prehybridization". Hybridization with the probe is achieved by transferring the filter to a probe-containing hybridization solution. The concentration of the probe in the solution may depend on the size of the probe. Usually the probe is used in excess. The hybridization temperature will depend upon the nature of the hybridization medium (the medium may affect the nucleic acid melting point). Optimum hybridization is generally considered to occur at the melting point of the nucleic acid minus approximately 20° C. In an aqueous medium, the temperature will normally be about 80° C. to 90° C. The duration of the incubation should be sufficient to allow substantially complete hybridization to occur. The hybridization will usually be complete within 12 to 24 hrs.

After the hybridization the support is washed with buffer (various degrees of stringency are used in the art) that normally contains a small amount of surfactant to remove unbound probe. After washing the presence of labeled duplexes on the filter is detected. The mode of detection will depend on the nature of the label. When the label is $^{32}$P, conventional β-emission detectors, e.g., scintillation counters, are used.

As an alternative to the filter hybridization assay described above, cytohybridization procedures may be used. In cytohybridizations the cells are fixed on a support such as a slide or cover slip and treated with alkali or heat to partially denature the cellular DNA. The labeled probe is then applied directly to the cells under conditions similar to those used in the filter hybridization.

Preparation of Anti-ARV Antibodies

Sera containing high titers of anti-ARV antibodies may be made by immunizing laboratory animals, e.g., rabbits, mice, guinea pigs, with ARV particles, infected HUT-78 cells, or immunogenic ARV proteins. The animal will typically be inoculated and boosted at least once with the antigen. Serum is collected from the host and its anti-ARV content determined by immunoassay using the original inoculant as antigen.

Anti-ARV monoclonal antibodies may be made by conventional somatic cell hybridization techniques using Ig-producing cells or precursors (lymphocytes, splenocytes) from immunized animals or humans having high titers of anti-ARV antibody and available tumor cell lines as fusion partners. Mice and murine myelomas are preferred because of their availability. These antibodies may be used to identify and isolate immunogenic ARV proteins by conventional techniques such as immunoassay and affinity chromatography. The proteins may be coupled (immobilized) to solid phases (e.g., beads made or polyvinylchloride, polystyrene, latex, etc.) for use in immunoassays. Purified proteins may be partially sequenced and the sequence information used to deduce nucleotide sequences for making probes to identify the ARV gene(s) that encode the protein(s). Once identified the genes may be isolated and cloned into expression vectors. These vectors may be used to transform competent hosts to produce transformants that are capable of producing the viral protein.

AIDS Vaccines

Vaccines may be made using inactivated forms of ARV virus or, preferably, ARV vaccine subunits (e.g., immunogenic ARV polypeptides or immunogenic fragments thereof). As used in this context the term "immunogenic" is intended to mean a polypeptide which upon introduction into humans causes an immune response in the recipient that results in the production of virus-neutralizing antibody. Depending upon the size of the polypeptides it may be desirable to confugate them to carrier proteins such as ovalbumin or serum albumin prior to their administration. The vaccine composition will include an immunogenic amount of the polypeptide, a parenteral vehicle, and, optionally, an immunopotentiator. The vaccine will be administered parenterally.

The following example further illustrates various aspects of the invention. This example is not intended to limit the invention in any manner.

Identification and Isolation of ARV

Peripheral mononuclear cell (PMC) cultures were established from 10–30 ml of heparinized blood from individuals seen at the Kaposi's Sarcoma Clinic, University of California, San Francisco (UCSF) or the AIDS Clinic, San Francisco General Hospital, USCF. All patients and most of the clinically healthy individuals were randomly selected and had lived in San Francisco for at least 2 years. The PMC were separated on Ficoll-Hypaque (F/H) gradients. After washing, cells were plated at approximately $2\times10^6$ cells/ml in RPMI 1640 containing 10% fetal bovine serum and antibiotics (100 u/ml penicillin, 100 µg/ml of streptomycin). To this medium was added interleukin-2 (IL-2) (0.5 µg/ml) (Meloy Laboratories, Springfield, Va.) and polybrene (1 µg/ml). At initiation of the cultures, approximately 2.5 µg/ml of phytohemagglutinin (PHA) (Wellcome Reagents, Ltd., England) was added. Some cultures also received $10^{-5}$M 2-mercaptoethanol and sheep anti-alpha interferon sera provided by the National Institutes of Health (Lot #61220), Dr. Kari Cantell, Helsinki, or Dr. Francoise Barre-Sinoussi, Paris. These anti-interferon sera were used at a dilution which neutralized 700–1000 units of alpha interferon/ml/culture. The culture supernatants were routinely assayed for $Mg^{++}$-dependent reverse transcriptase (RT) activity every 3–6 days using the following procedure.

Culture medium (1–5 ml) from PMC was spun at 40,000 rpm, 4° C., 45 min, in a Beckman SW41 rotor. The pellets were assayed in a 50 µl reaction containing: 40 mM Tris-HCl pH 7.8; 60 mM KCl; 2.2 mM dithiothreitol; 10 mM $MgCl_2$; 0.1% Triton X-100; 30 µCi of [$^3$H]-TTP (spec. act. 78 Ci/mM) and 50 µg/ml of poly(rA)oligo(dT) (PL Biochemicals). Samples were incubated at 0° C. for 15 min; the reaction was then run for 1 hr, 37° C., and stopped with 4 ml of 5% trichloroacetic acid/0.005M Napyrophosphate/0.5N HCl. Precipitates were collected on Whatman GF/A filters, washed, dried and counted in an LKB liquid scintillation counter. FIG. 1 shows the graph of the results for a representative culture. As shown, a high level of RT activity was noted in the culture on the 15th day. On day 22 (arrow), when the RT level was low, the supernatant fluid was removed and inoculated onto fresh human PMC stimulated 3 days before with PHA. Supernatants from this culture, within six days, contained RT activity at levels of 650,000 cpm/ml and yielded the virus isolate, ARV-2.

The results of RT activity tests on all PMCs tested are reported in Table 1.

TABLE 1

Detection of ARV in AIDS Patients and Other Individuals from San Francisco

| Diagnosis | Number Positive Number Tested | % Positive |
|---|---|---|
| AIDS with Kaposi's sarcoma | 22/41 | 53.6 |
| AIDS with opportunistic infection | 0/4 | 0 |
| Lymphadenopathy Syndrome | 5/10 | 50.0 |
| Sexual male contacts of AIDS patients* | 3/14 | 21.4 |
| Clinically healthy homosexual men | 2/9 | 22.2 |
| Clinically healthy heterosexual individuals | 1/23 | 4.0 |

*Steady sexual contact with a patient for at least 6 months before the onset of his disease.

As reported, in cultures prepared from 41 homosexual AIDS patients, 22 were positive for $Mg^{++}$-dependent (RT) activity. The viruses were found primarily in PMC of patients in the early stages of disease. The RT activity was detected in the PMC usually within the first two weeks of culture with the peak of activity observed by 12–16 days (FIG. 1). When bone marrow aspirates were cultured, 3 out of 9 cultures from AIDS patients showed evidence of retroviruses. With some cell cultures, the use of anti-interferon antiserum helped demonstrate the presence of virus. When RT activity diminished in the cultures after 2–3 weeks, the addition of fresh lymphocytes from normal donors would sometimes reestablish RT activity. Supernatant fluids from positive cultures (some stored at −70° C. for over 3 months) also induced RT activity in uninfected fresh lymphocyte cultures. $Mg^{++}$-dependent RT activity was also observed repeatedly in PMC cultures from patients with lymphadenopathy syndrome (LAS), steady sexual male contacts of AIDS patients, clinically healthy homosexual men, and in one healthy young heterosexual man.

The viruses detected in seven of the PMC cultures were grown in high titer and had similar characteristics. ARV-2, mentioned previously, was recovered within 2 weeks directly from the PMC of a patient approximately one month prior to the onset of AIDS. ARV were isolated from subsequent cultures taken two and six months later, after the onset of AIDS. Multiple time spaced samplings from 5 out of 6 other patients with AIDS have also yielded retroviruses.

Further Characterization

A. Density of ARV Particles

Figure 2:
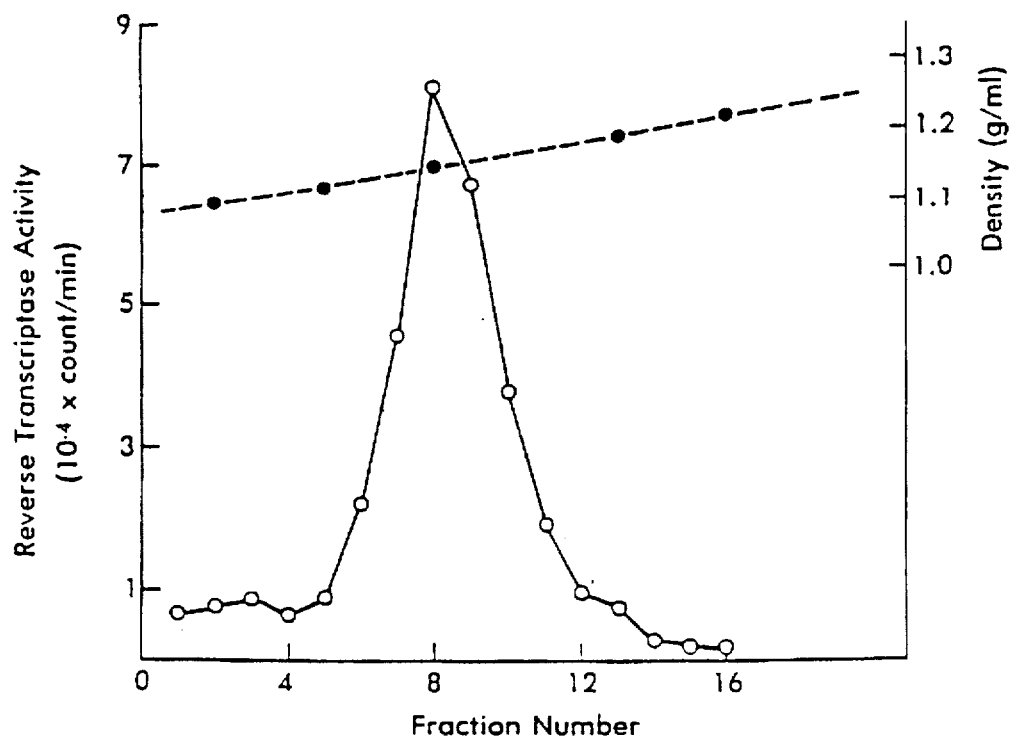
FIG. 2 is a graph of the sucrose gradient of the example, infra.

Supernatant from a culture of ARV-infected PMC was concentration by centrifugation in a Beckman SW55 rotor (45,000 rpm, 4° C., 30 min). The pellet was resuspended in 100 μl of TNE (10 mM Tris-HCl pH 8.0; 100 mM NaCl; 1 mM EDTA pH 8.0) and layered on a 20%–60% (by weight) sucrose gradient in TNE and centrifuged in a Beckman SW55 rotor (35,000 rpm, 4° C., 16 hr). 200 μl fractions were collected from the top and assayed for RT activity. Density of sucrose was determined by refractive index measurements. The RT activity of the viruses was associated with particles banding at 1:14 to 1:16 g/ml (FIG. 2).

B. $Mg^{++}$ Preference

The viral enzyme, using poly(rA):oligo dT or poly(rC):oligo dG as template primers, had up to an eight-fold cation preference for $Mg^{++}$ over $Mn^{++}$. With $Mg^{++}$, RT levels higher than $3.5 \times 10^6$ cpm/ml of culture supernatant could be reached.

C. Effect on Multinucleated Cells

The isolated viruses induced multinucleated cells in lymphocyte cultures. They did not immortalize the cells.

D. Morphology

EM analysis of thin sections of PMCs producing ARV were made. Cells were fixed in glutaraldehyde, washed and post fixed in osmium tetroxide and embedded in Araldite. Thin sections were stained in uranyl acetate and lead citrate. Particles with characteristic type D retrovirus morphology were detected. Budding forms showed early features of both type C and type D particles, but only mature type D particles were observed in the cultures.

E. Serology

Cell cultures infected with the seven ARV isolates were studied for cross-reactivity with anti-HTLV-I and anti-LAV antibodies by standard indirect immunofluorescence assays (IFA) using fluorescein-labeled goat anti-mouse IgG or goat anti-human IgG. In these assays, cells were spotted onto glass slides, air dried and fixed in cold acetone for 15 min. An HTLV p19 monoclonal antibody provided by Drs. Robert-Guroff and Gallo, NIH, and an ATLV p19/p28 monoclonal antibody provided by Dr. Y. Hinuma, Kyoto, Japan were used. For detection of LAV, human serum (BRU) provided by Dr. Barré-Sinoussi, Paris was used. Only the anti-LAV antibody reacted with the cells with up to 20% of the cells exhibiting cross-reactivity.

Sera (heated at 56° C., 30 min, used at 1:10 dilution) from AIDS patients and other individuals from San Francisco were tested for the presence of anti-ARV antibodies by a similar IFA using a HUT-78 line containing 40% of the cells infected with ARV-2. The results of these tests are reported in Table 2 below.

TABLE 2

Antibodies to ARV in Sera From AIDS Patients and Other Individuals from San Francisco#

| Diagnosis | Anti-ARV |
|---|---|
| AIDS with Kaposi's sarcoma (KS) | 59*/67 (88%) |
| AIDS with opportunistic infection | 18/18 (100%) |
| Lymphadenopathy Syndrome (LAS) | 22*/27 (81%) |
| Sexual male contacts of AIDS patients | 11/12 (92%) |
| Clinically healthy homosexual men | 27*/47 (57%) |
| Clinically healthy heterosexual individuals | 0*/53 (0%) |

FIG. expressed as number positive/number tested (% positive)
*When antibody negative sera were tested at a 1:5 dilution against the ARV-infected cells, 8/9 AIDS, 3/5 LAS patients, and 2/12 healthy homosexual controls showed reactivity; none of the sera from healthy heterosexual individuals was positive at this dilution.

These results indicate a very high prevalence of antibodies to ARV in sera from patients with AIDS and LAS, and in sera from steady sexual contacts and healthy homosexual men. When the antibody negative sera from patients with AIDS and LAS were tested at a lower dilution, all but 2 reacted with the ARV-infected cells. No antibodies were detected in the sera of randomly selected healthy heterosexual men from San Francisco. All available sera of individuals from whom ARVs were isolated had antibodies to the virus. Some patients' sera titered 1:640. The high frequency of antibodies in healthy homosexuals may reflect a bias from some who volunteered for these studies. Nevertheless, these results indicate the very close association of ARV with AIDS and LAS, its widespread presence in the homosexual community, and the greater detection of antibodies to ARV than infectious virus. The data support the contention that LAS is related to AIDS.

Modifications to the above-described modes for carrying out the invention that are obvious to those of skill in medicine (particularly infectious diseases), immunology, biochemistry, genetic engineering and related fields are intended to be within the scope of the following claims.

I claim:

1. A polynucleotide hybridization assay for determining the presence of an AIDS-associated virus having the identifying characteristics of the AIDS-associated virus found in the HUT-78 cell line having an ATCC accession no. of CRL 8578 in a patient comprising:
   (a) liberating polynucleic acids from a sample of leukocytes from a patient and rendering the liberated polynucleic acids single-stranded, if necessary;
   (b) transferring the liberated polynucleic acids to a solid support under conditions that immobilize them on the support;
   (c) hybridizing the immobilized liberated polynucleic acids with a labeled single stranded reverse transcribed DNA of the genomic RNA of said AIDS-related virus or a labeled fragment of said DNA;
   (d) detecting the presence of immobilized labeled polynucleic acids duplexes on the support; and
   (e) relating said present of said immobilized labeled polynucleic acids duplexes to the presence of said AIDS-related virus.

2. A cytohybridization assay for determining the presence of an AIDS-related virus having the identifying characteristics of the AIDS-related virus found in the HUT-78 cell line having an ASTCC accession no. of CRL 8578 in a patient comprising:
   (a) fixing a sample of leukocytes from the patient on a support;
   (b) treating the fixed cells so as to denature cellular DNA;
   (c) hybridizing the denatured cellular DNA with a labeled single stranded reverse transcribed DNA of the genomic RNA of said AIDS-related virus or a labeled fragment of said DNA;
   (d) detecting the presence of labeled polynucleic acid duplexes in the fixed cells; and
   (e) relating said presence of said immobilized labeled polynucleic acids duplexes to the presence of said AIDS-related virus.

3. The hybridization assay according to claim 1, wherein said leukocytes are peripheral blood lymphocytes.

4. The cytohybridization assay according to claim 2, wherein said leukocytes are peripheral blood lymphocytes.

5. A polynucleotide hybridization assay for determining the presence of an AIDS-related virus in a patient, wherein said AIDS related virus has the identifying characteristics of the AIDS-related virus found in the HUT-78 cell line having an ATCC accession no. of CRL 8578, said assay comprising:
   (a) liberating polynucleic acids of said AIDS-related virus from a sample of lyphocytes from a patient and rendering the liberated polynucleic acids single-stranded, if necessary;
   (b) transferring the liberated polynucleic acids to a solid support under conditions that immobilize them on the support;
   (c) labeling said liberated polynucleic acids by hybridization with probe;
   (d) detecting the presence of said labeled liberated polynucleic acids; and
   (e) relating said presence of said labeled liberated polynucleic acids to the presence of said AIDS-related virus is said patient.

* * * * *

UNITED STATES PATENT AND TRADEMARK OFFICE

CERTIFICATE OF CORRECTION

PATENT NO. : 5,736,328

DATED : April 7, 1998

INVENTOR(S) : Jay A. Levy

It is certified that error appears in the above-identified patent and that said Letters Patent is hereby corrected as shown below:

Column 3, line 38   after "ARV-2" insert --and identified on the submission form as E line--

Column 3, line 40   "9 Aug." should read --7 Aug.--

Column 9, line 9    "8578" should read --8597--

Signed and Sealed this

Seventh Day of July, 1998

Attest:

BRUCE LEHMAN

Attesting Officer    Commissioner of Patents and Trademarks